United States Patent [19]

Calabrese

[11] Patent Number: 4,677,969
[45] Date of Patent: Jul. 7, 1987

[54] CERVICAL COLLAR PERMITTING TRACHEOTOMY

[75] Inventor: Anthony Calabrese, Philadelphia, Pa.

[73] Assignee: Charles Griener and Company, Inc., Westville, N.J.

[21] Appl. No.: 794,258

[22] Filed: Nov. 1, 1985

Related U.S. Application Data

[63] Continuation of Ser. No. 656,123, Sep. 28, 1984, abandoned, which is a continuation-in-part of Ser. No. 520,083, Aug. 4, 1983, Pat. No. 4,515,153.

[51] Int. Cl.⁴ .............................................. A61H 1/02
[52] U.S. Cl. .................................. 128/75; 128/76 R; 128/87 B; 128/DIG. 23
[58] Field of Search ............... 128/75, 87 B, DIG. 23, 128/76 R, 78; D24/64; 2/44, 45, 410, 425

[56] References Cited
U.S. PATENT DOCUMENTS
4,582,051 4/1986 Greene et al. .................... 128/87 B OTHER PUBLICATIONS
DePuy reference "Philadelphia Cervical Collar", copyright 1983.

Primary Examiner—Richard J. Apley
Assistant Examiner—H. Macey
Attorney, Agent, or Firm—Seidel, Gonda, Goldhammer & Abbott

[57] ABSTRACT

A cervical collar having front and rear halves removably connected together provides for the possibility of a tracheotomy via an opening in the front half so as to permit access to a person's trachea. The collar provides sufficient support so as to restrict the cervical region without hyperextension of the neck thereby avoiding further injury.

6 Claims, 5 Drawing Figures

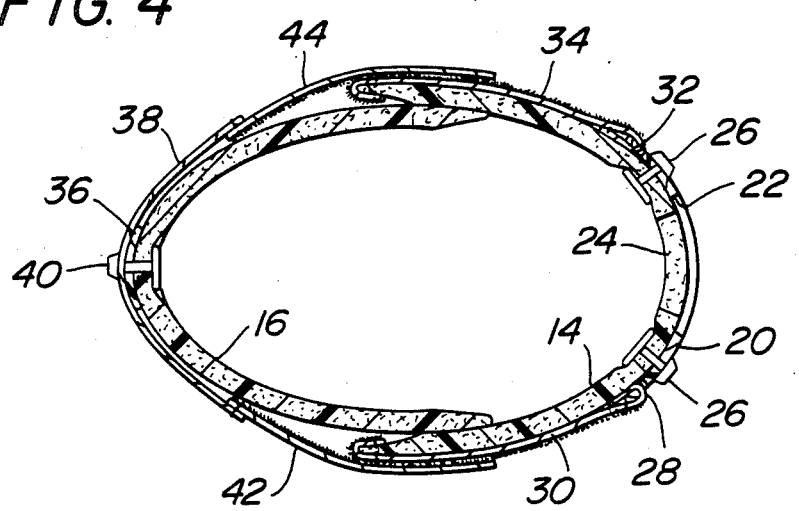

4,677,969

CERVICAL COLLAR PERMITTING TRACHEOTOMY

This application is a continuation of my U.S. application Ser. No. 656,123, filed Sept. 28, 1984 and entitled "Cervical Collar Permitting Tracheotomy" and now abandoned. Application Ser. No. 656,123 is a continuation-in-part of my U.S. application Ser. No. 520,083, filed Aug. 4, 1983 and entitled "Stabilizer For Cervical Collar" and which is now U.S. Pat. No. 4,515,153 granted May 7, 1985.

BACKGROUND OF THE INVENTION

Cervical collars are well-known. See U.S. Pat. No. 3,756,226 dated Sept. 4, 1973. The collar disclosed in said patent is comprised of body halves removably coupled together. At the center of the front half of the collar disclosed in said patent, there is provided a rigid reinforcing support member directly opposite a person's trachea. Hence, in the event that an emergency tracheotomy is called for, there is no way to have access to the trachea without removing the front half of the collar.

The present invention is directed to a solution of the problem of how to provide a cervical collar which provides sufficient support so as to restrict the cervical region of a patient at the scene of an accident without hyperextension of the neck and permits a tracheotomy without otherwise interfering with the provision of rigid reinforcing members on the collar halves.

SUMMARY OF THE INVENTION

The present invention is directed to a cervical collar which permits a tracheotomy. The cervical collar is comprised of first and second discrete body halves. Each body half is generally U-shaped and preformed from a soft flexible, light weight foam polymeric material. A strap means is provided for releasably interconnecting the free ends of the halves in overlapping relation. Each half has a rigid support member fixedly secured thereto adjacent the bight. The rigid support member on the front half is positioned so as to expose a hole at the bight of the front half for permitting a tracheotomy without interfering with the interconnection between the halves when worn by a patient.

It is an object of the present invention to provide a novel cervical collar which may be used with or without a stabilizer for providing any necessary support and while permitting a tracheotomy without removing the collar.

Other objects will appear hereinafter.

For the purpose of illustrating the invention, there is shown in the drawings a form which is presently preferred, it being understood, however, that this invention is not limited to the precise arrangements and instrumentalities shown.

FIG. 4 is a sectional view taken along the line 4—4 in FIG. 3.

DETAILED DESCRIPTION

Figure 1:
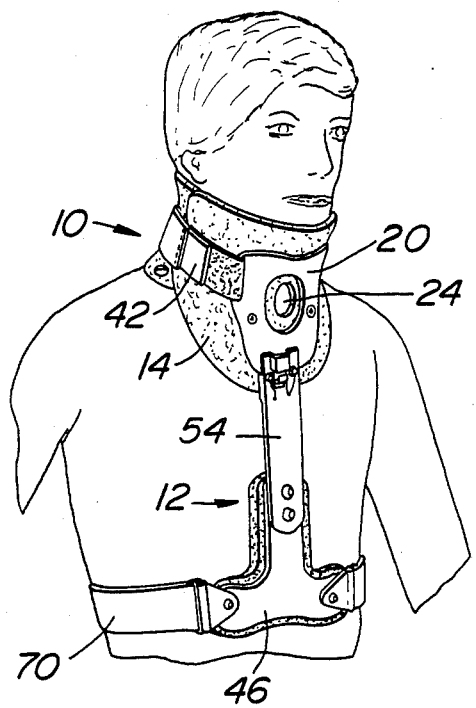
FIG. 1 is a perspective view of a person wearing a stabilized cervical collar in accordance with the present invention.
Figure 3:
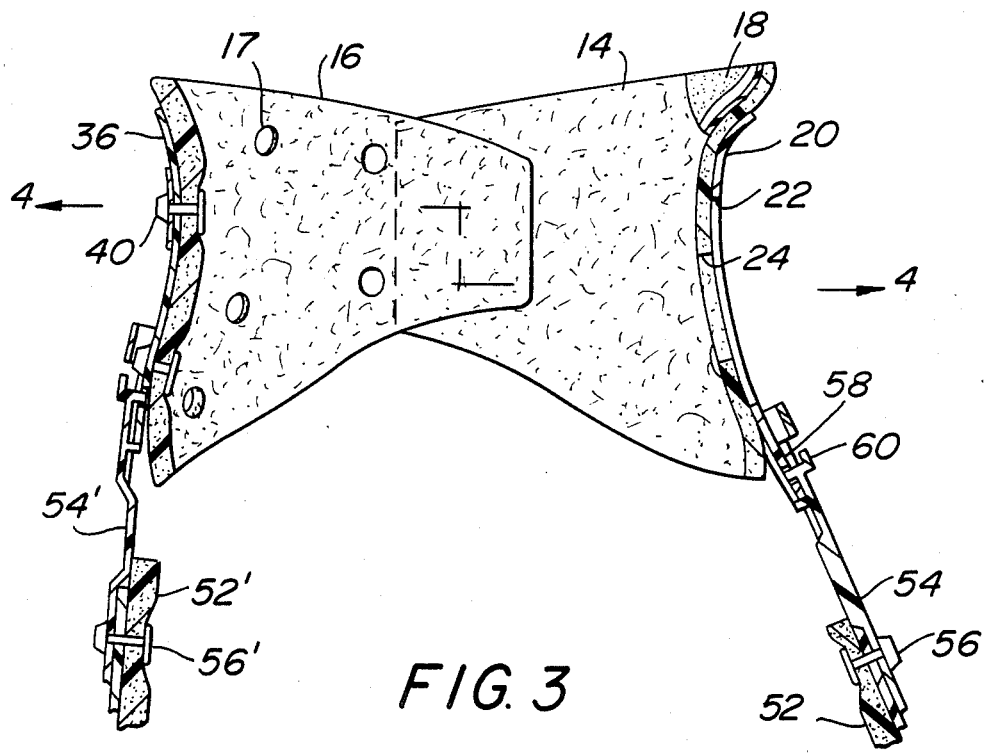
FIG. 3 is a sectional view taken along the line 3—3 in FIG. 2.

Referring to the drawing in detail, wherein like numerals indicate like elements, there is shown in FIG. 1 a cervical collar designated generally as 10 which may be utilized with or without a stabilizer designated generally as 12. Collar 10 without the stabilizer is shown in FIG. 6. The collar 10 is comprised of a front half 14 and a rear half 16. Each collar half is generally U-shaped and preformed from a soft, flexible, light-weight closed cell foam polymeric plastic material. The halves overlap one another as shown more clearly in FIGS. 2–4 and may have air holes 17 therethrough.

The front half 14 has a chin cavity 18 at the bight. The chin cavity 18 is preferably covered with a material such as moleskin which is adhesively or otherwise secured to the cavity 18. The front half 14 is provided with a rigid reinforcing support member 20 at the bight. Member 20 has an opening 22 which surrounds a smaller diameter opening 24 in the front half at the bight thereof. Opening 24 has a preferred diameter of about one and one half inches (3.8 cm). Opening 24 is positioned so as to be directly opposite the trachea when collar 10 is worn by a patient as shown in FIG. 1.

Figure 2:
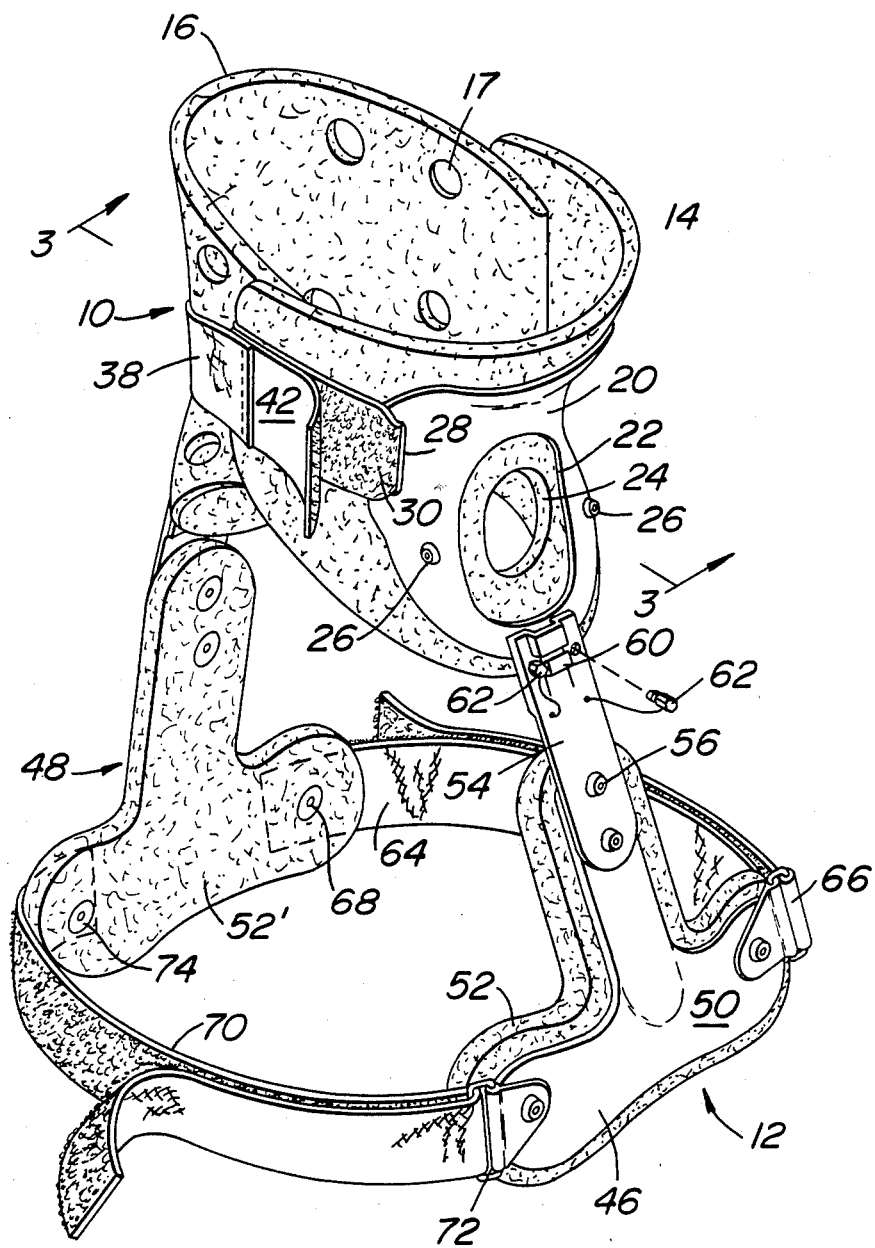
FIG. 2 is a perspective view of the stabilized collar shown in FIG. 1.
Figure 5:
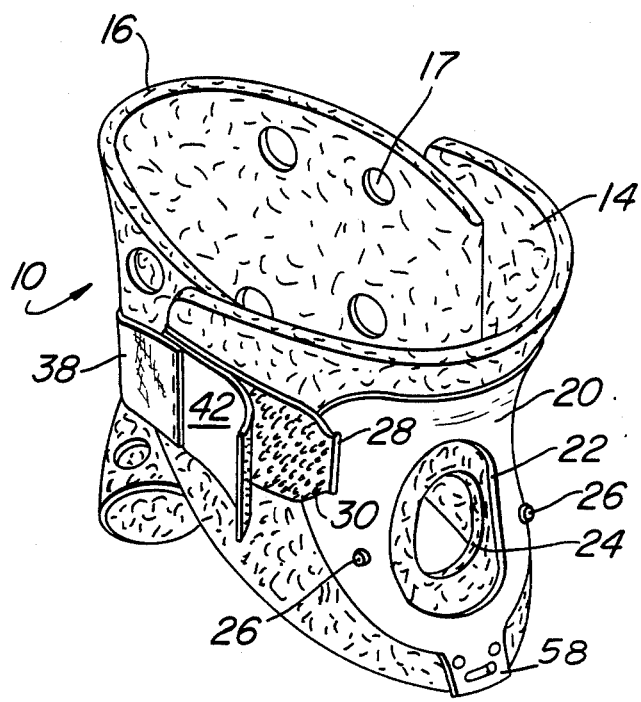
FIG. 5 is an enlarged perspective view of the collar shown in FIG. 1 without the stabilizer.

The member 20 is secured to the front half 14 by a plurality of plastic rivets 26. As shown more clearly in FIG. 4, the member 20 is arcuate so as to conform to the arcuate surface of the front half 14 adjacent its bight. As shown in FIGS. 2 and 4, along one side edge of the member 20, there is provided a slot through which extends one end portion of a strap 30. The strap 30 extends along the front half 14 to the free end thereof wherein the strap is stitched to the front half 14. On other side of the member 20, there is provided a similar slot 32 through which extends one end portion of a strap 34. The other end of the strap 34 is stitched to a free end of the front half 14.

As shown more clearly in FIG. 4, at the bight of the rear half 16, there is provided a rigid reinforcing support member 36 attached thereto by a plastic rivet 40. A strap 38 is also attached to the rear half 16 by said rivet 40.

A strip 42 is attached to one end of the strap 38 and is adapted to overlie a portion of the strap 30 in the assembled relationship of the collar 10. A strip 44 is attached to the other end of strap 38 and is adapted to overlie a portion of strap 34 in the assembled position of the collar 10. The outer surface of straps 30, 34 and the inner surface of the strips 42, 44 have mating structure adapted for releasable engagement. Such mating structure may be of the type which is sold commercially under the trademark VELCRO.

The stabilizer 12 includes a front piece 46 adapted to overlie part of a persons's chest and a rear piece 48 adapted to overlie a person's back. The front piece and the rear piece are identical except as will be made clear hereinafter. Hence, only the front piece 46 will be described in detail. Corresponding prime numerals are provided on the rear piece 48.

The front piece 46 includes a substrate 50 of rigid materially having a generally T-shape. The substrate 50 is preferably made from a rigid polymeric plastic material such as ABS. A liner 52 is adhesively or otherwise secured to the curved innersurface of substrate 50. The liner 52 is preferably made from a closed cell of foam material such as polyethylene so as to have the following attributes: uniform thickness, non-toxic, low specific gravity of about 0.04, corrosive, and will not burn but will melt. The shape of liner 52 corresponds to the shape of substrate 50.

A connecting member 54 is fixedly connected to the center leg of substrate 50 in any convenient manner such as by plastic rivets 56. The connecting member 54 is preferably made from a softer or more flexible plastic material than the substrate 50 such as polyethylene.

Member 54 is arcuate at its lower end and channel-shaped at its upper end. Member 54 is telescoped over a downwardly extending extension member 58 on the member 20 until a tongue on member 60 snaps into a slot on member 58. Member 60 acts like a hinge and is integral at one end only with the member 54.

It is desirable to removably interconnect the front and rear pieces 46, 48 to the halves of the collar 10 in a manner so that stabilizer 12 is not readily removable by the patient. In this regard, at least one and preferably two plastic rivets 62 are carried by member 54 by way of a flexible string. The rivets 62 are easily pushed and snapped into aligned holes on members 54 and 58. Each rivet preferably is provided with a head having flats on opposite sides thereof and split shanks. The rivets 62 are easily force-fit into the aligned holes by application of finger pressure. However, a tool such as a pair of pliers is needed to pull out the rivets. Rivets 62 are designed so that they cannot be removed by the patient and should only be removed when authorized by a physician. When the rivets 62 are removed, members 54 and 58 are easily separated by pulling on the member 60 so as to cause removal of its tongue from the slot in member 58. The channelshape at the upper end of member 54 assures that the tongue of member 60 will be aligned with the mating slot in member 58.

The rear piece 48 is identical with the front piece 46 except as follows. Corresponding elements are provided with corresponding primed numerals. Member 54' is thinner and therefore more flexible than member 54. Greater rigidity is needed on the front peice 46 as compared with the rear piece 48. The upper end of member 54 is removably connected to the reinforcing support member 36 on the rear half 16 in the same manner as described above.

A strap 64 has one end fixedly secured to the substrate on the rear piece 48 by a plastic rivet 68. The strap 64 extends through a plastic loop 66 on the front piece 46 and then overlies itself. Juxtaposed surfaces of the strap 64 are provided with adjustable fasteners which are preferably of the VELCRO type.

A strap 70 is similarly provided to interconnect the front and rear pieces 46, 48 on the opposite side from strap 64. One end of strap 70 is fixedly secured to the substrate on the rear piece 48 by a plastic rivet 74. An intermediate portion of strap 70 extends through a plastic loop 72 on the front piece 46 and then overlies itself. Juxtaposed surfaces on strap 70 are provided with adjustable fasteners as described above.

The collar 10 may be worn by a patient when required due to a particular injury and with advice of a physician. If the particular injury requires increased stabilization of the collar 10, so as to prevent hyperextending the patient's neck, the stabilizer 12 is removably connected to the reinforcing members on the front half 14 and rear half 16. When no longer required, the stabilizer 12 may be removed while collar 10 remains on the patient. When an injury requires wearing of the collar 10 and requires a tracheotomy, the trachea is readily accessible through the opening 24. If the opening 24 is too small or is not aligned with the trachea, the foam of front half 14 may be readily cut at the scene of an accident and enlarged up to the size of the opening 22. The opening 24 facilitates a tracheotomy without removing the collar 10 and regardless of whether or or not the stabilizer 12 is removably attached to the collar 10.

Since patients come in different sizes, the collar 10 is preferably made in different sizes such as small, medium and large. All of the rivets described above and shown in drawings are preferably made from plastic whereby a patient may be X-rayed with the collar of the present invention mounted on the patient. There are no metal parts which will show up on X-rays and interfere with evaluation of the X-rays.

An advantage of the collar 10 is that is can facilitate a life-saving tracheotomy at the scene of an accident. When additional support is needed, stabilizer 12 can be removably attached to the collar 10 at the scene of the accident or later at a hospital with removing collar 10. The bight on the front half of the collar has been sufficiently reinforced to provide the necessary support without interfering with the access hole needed for tracheotomy.

Thus, there is provided a versatile device for use in an emergency by a paramedic in the field. Collar 10 provides the required support in the cervical region and can be applied quickly without the necessity of any tools.

The present invention may be embodied in other specific forms without departing from the spirit or essential attributes thereof and accordingly, reference should be made to the appended claims, rather than to the foregoing specification, as indicating the scope of the invention.

I claim:

1. A cervical collar suitable for use with a stabilizer having a connecting member with a tongue resiliently connected thereto and a hole for receipt of a rivet, said collar comprising:

first and second discrete collar halves, one of said collar halves being a front half and the other being a rear half, each collar half being U-shaped and having a bight portion and side portions and being formed of a soft flexible light-weight polymeric plastic material;

a first rigid support means secured to and located adjacent a bight portion of the front collar half;

a second rigid support means secured to and located adjacent the bight portion of the rear collar half;

means for removably interconnecting the free ends of the collar halves in overlapping relation; and each of said first and second rigid support means including a lower portion adapted to releasably secure the stabilizer thereto, each lower portion includes an alignment means and a fastening means, said alignment means includes a tab which is an extension of said lower portion, said tab having a width less than said lower portion, said tab having a slot extending into said tab, said slot adapted to receive the tongue on said stabilizer, and said fastening means includes an opening through said tab and spaced from said slot and adapted to receive the rivet whereby when the tongue engages said slot, the opening and hole are coaxially aligned.

2. A cervical collar suitable for use with a stabilizer having a connecting member with a tongue resiliently connected thereto and a hole for receipt of a rivet, said collar comprising:

first and second discrete collar halves, one of said collar halves being a front half and the other being a rear half, each collar half being U-shaped and having a bight portion and side portions and being preformed from a soft, flexible, light-weight polymeric plastic material;

a first rigid support means secured to and located adjacent the bight portion of the front collar half and including a widened upper portion extending across the bight portion and terminating proximal the side portions;

a second rigid support means secured to and located adjacent the bight portion of the rear collar half;

means for removably interconnecting the free ends of the collar halves in overlapping relation; and each of said first and second rigid support means including a lower portion adapted to releasably secure the stabilizer thereto, each lower portion includes an alignment means and a fastening means, said alignment means includes a tab which is an extension of said lower portion, said tab having a width less than said lower portion, said tab having a slot extending into said tab, said slot adapted to receive the tongue on said stabilizer, and said fastening means includes an opening through said tab and spaced from said slot and adapted to receive the rivet whereby when the tongue engages said slot, the opening and hole are coaxially aligned.

3. The cervical collar according to claim 2 wherein said front half is provided with an opening at the bight portion, and said first rigid support means is provided with an opening in juxtaposition with said opening in said front collar half bight portion.

4. A cervical collar suitable for use with a stabilizer having a connecting member with a tongue resiliently connected thereto and a hole for receipt of a rivet, said collar comprising:

first and second discrete collar halves, one of said collar halves being a front half and the other being a rear half, each collar half being U-shaped and having a bight portion and side portions and being preformed from a soft, flexible, light-weight polymeric plastic material, said front collar half having an opening at said bight portion;

a first rigid support means being secured to and located adjacent said bight portion of said front collar half and including a widened upper portion extending across said bight portion and terminating proximal said side portions, and a narrower central portion having an opening circumscribing and larger than said opening in said front collar half, a lower portion narrower than said upper and central portions and adapted to releasably secure the stabilizer thereto;

a second rigid support means being secured to and located adjacent said bight portion of said rear collar half, said second rigid support means having a lower portion adapted to releasably secure the stabilizer thereto;

means for removably interconnecting the free ends of said collar halves in overlapping relationship; and each said lower portion includes a tab provided with a slot adapted to receive a tongue on the stabilizer.

5. The cervical collar according to claim 4 wherein each support means lower portion includes an opening adapted to receive a rivet.

6. A cervical collar comprising:

first and second discrete collar halves, one of said collar halves being a front half and the other being a rear half, each collar half being U-shaped and having a bight portion and side portions and being preformed of a soft, flexible light-weight polymeric material, said front collar half having an opening at said bight portion;

a first rigid support means being secured to and located adjacent said bight portion of said front collar half and including a widened upper portion extending across said bight portion and terminating proximal said side portions, and a narrow central portion having an opening circumscribing and larger than said opening in said front collar half, and a lower portion narrower than said upper and central portions and adapted to releasably secure a stabilizer thereto;

a second rigid support means being secured to and located adjacent said bight portion of said rear collar half, said second rigid support means including a lower portion adapted to releasably secure said stabilizer thereto;

means for removably interconnecting the free ends of said collar halves in overlapping relation;

said stabilizer for said collar adapted for preventing any movement of a patient's head, said stabilizer including a front piece adapted to overlie a part of a person's chest and a rear piece adapted to overlie a part of a person's back;

means on the upper end of said stabilizer for releasably interconnecting the upper end of the front piece with said first support means and means on said upper end of said rear piece for removably interconnecting the rear piece with the second support means, said means including a connecting member with a tongue resiliently connected thereto and a hole for receipt of said rivet; and each lower portion of said first and second rigid support means includes an alignment means and a fastening means, said alignment means includes a tab which is an extension of said lower portion, said tab having a width less a tab which is an extension of said lower portion, said tab having a width less than said lower portion, said tab having a slot extending into said tab, said slot adapted to receive the tongue on said stabilizer, and said fastening means includes an opening through said tab and spaced from said slot and adapted to receive the rivet whereby when the tongue engages said slot, the opening and hole are coaxially aligned.

* * * * *